United States Patent
Klimek et al.

(10) Patent No.: US 9,579,137 B2
(45) Date of Patent: Feb. 28, 2017

(54) GRAFT DELIVERY SYSTEM AND METHODS THEREOF

(71) Applicant: GLOBUS MEDICAL, INC, Audubon, PA (US)

(72) Inventors: Jennifer Klimek, King of Prussia, PA (US); Allison Adams, Philadelphia, PA (US); Daniel Laskowitz, Lancaster, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 149 days.

(21) Appl. No.: 14/451,653

(22) Filed: Aug. 5, 2014

(65) Prior Publication Data

US 2015/0045889 A1 Feb. 12, 2015

Related U.S. Application Data

(60) Provisional application No. 61/862,833, filed on Aug. 6, 2013.

(51) Int. Cl.
*A61F 2/46* (2006.01)
*A61B 17/88* (2006.01)
*A61F 2/44* (2006.01)

(52) U.S. Cl.
CPC ........ *A61B 17/8822* (2013.01); *A61F 2/4601* (2013.01); *A61F 2/4644* (2013.01); *A61B 2017/8838* (2013.01); *A61F 2/442* (2013.01); *A61F 2002/4475* (2013.01); *A61F 2002/4645* (2013.01)

(58) Field of Classification Search
CPC .................................................... A61F 2/4601
See application file for complete search history.

(56) References Cited

U.S. PATENT DOCUMENTS

| | | | | |
|---|---|---|---|---|
| 2003/0036762 A1* | 2/2003 | Kerr | ................... | A61B 17/3472 606/93 |
| 2003/0187445 A1* | 10/2003 | Keith | ................. | A61B 17/0401 623/17.11 |
| 2004/0260303 A1* | 12/2004 | Carrison | ............ | A61B 17/3472 606/92 |
| 2007/0213655 A1* | 9/2007 | Prusmack | .......... | A61B 17/3472 604/57 |
| 2011/0230970 A1* | 9/2011 | Lynn | ....................... | A61F 2/442 623/17.16 |
| 2011/0301712 A1* | 12/2011 | Palmatier | .............. | A61F 2/4455 623/17.16 |
| 2013/0345710 A1* | 12/2013 | Kleiner | ................. | A61F 2/4455 606/94 |
| 2014/0330315 A1* | 11/2014 | Butler | ................ | A61B 17/7085 606/278 |

* cited by examiner

*Primary Examiner* — Nicholas Plionis

(57) ABSTRACT

The present invention relates to minimally invasive graft delivery systems and devices. The systems and devices provide a means to deliver graft material minimally invasively, such as to a spacer within a disc space. A particular system can include a cannula, a syringe and an extrusion tool. The extrusion tool can be used to extrude material from the cannula and syringe, and can have multiple modes of operation to accommodate the extrusion of materials of different viscocities.

20 Claims, 12 Drawing Sheets

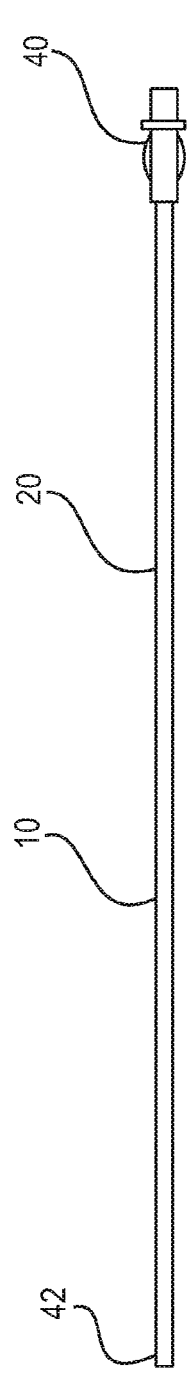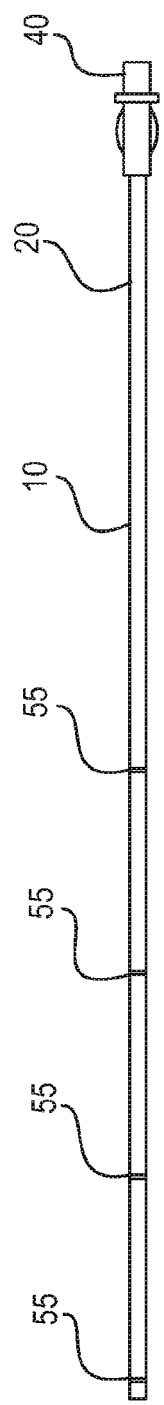
*FIG. 1*  *FIG. 2*

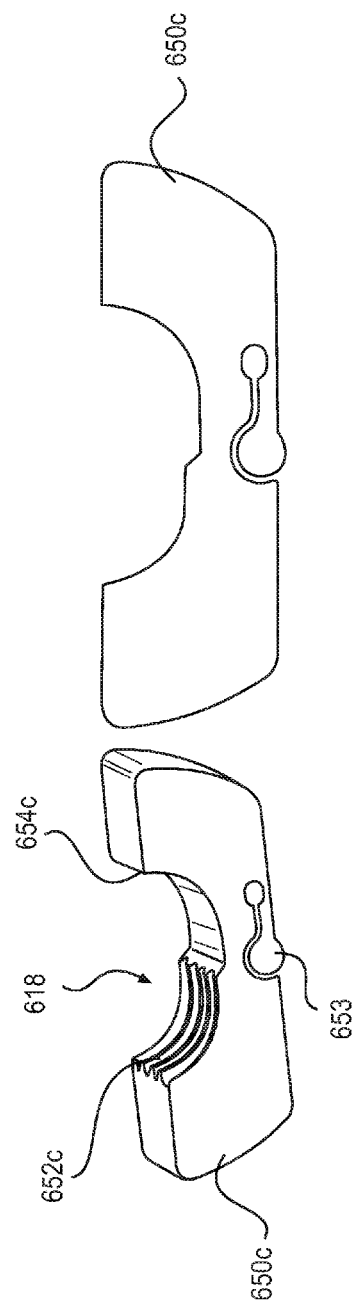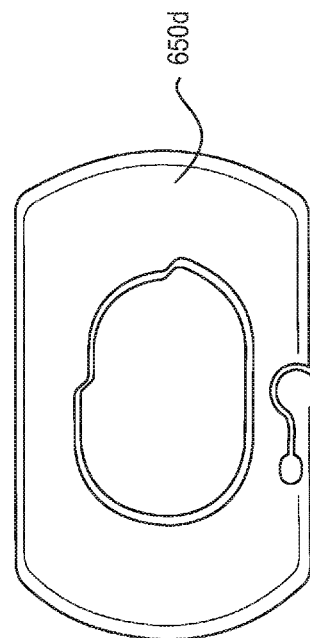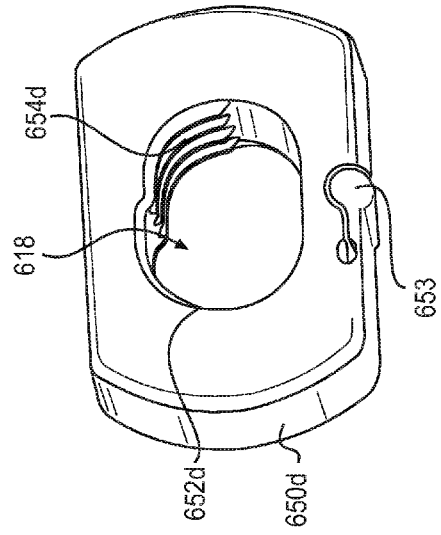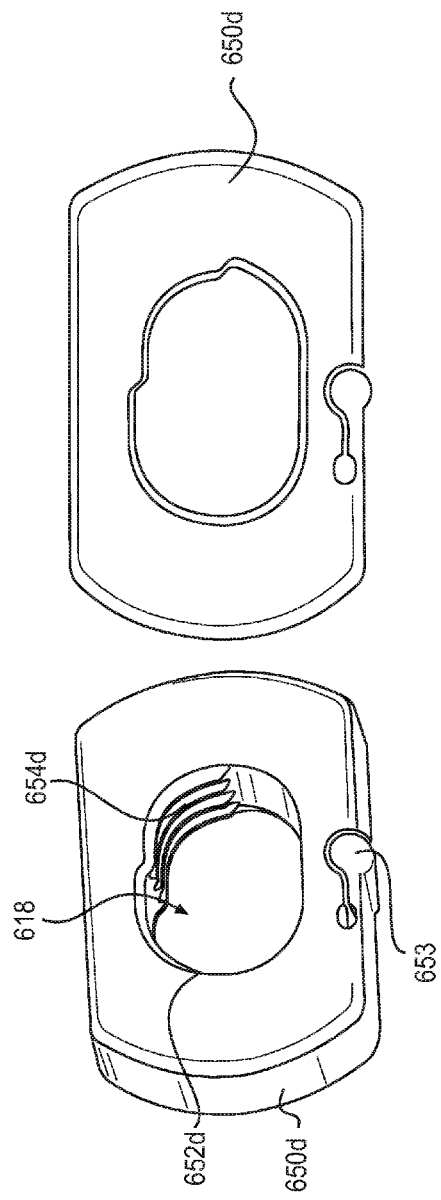

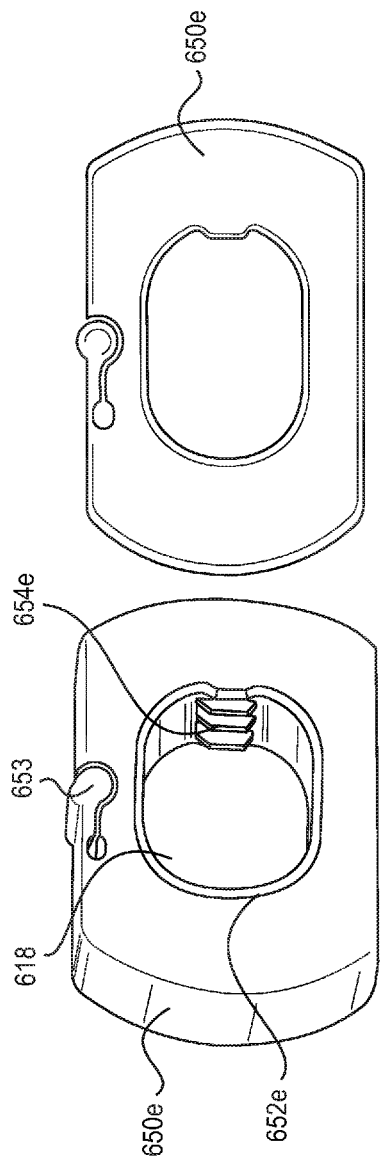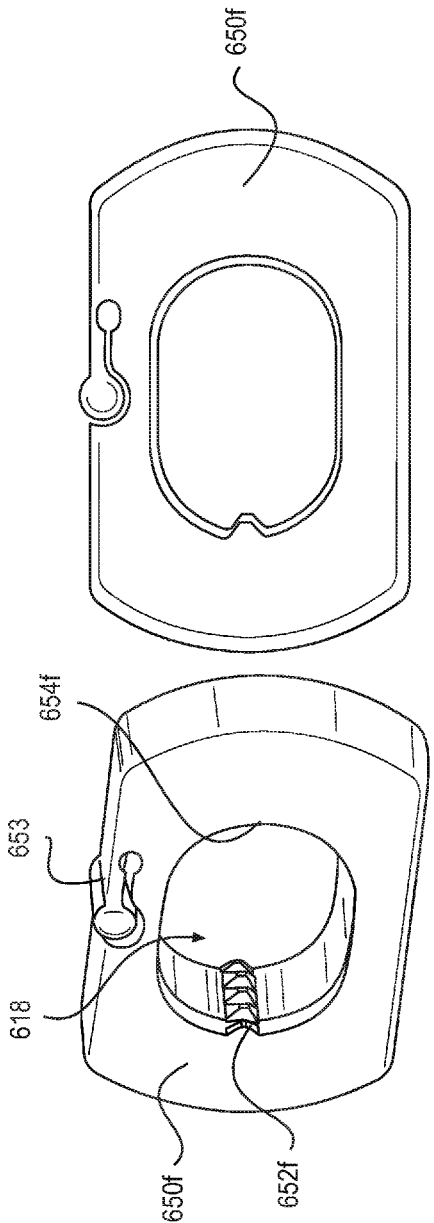

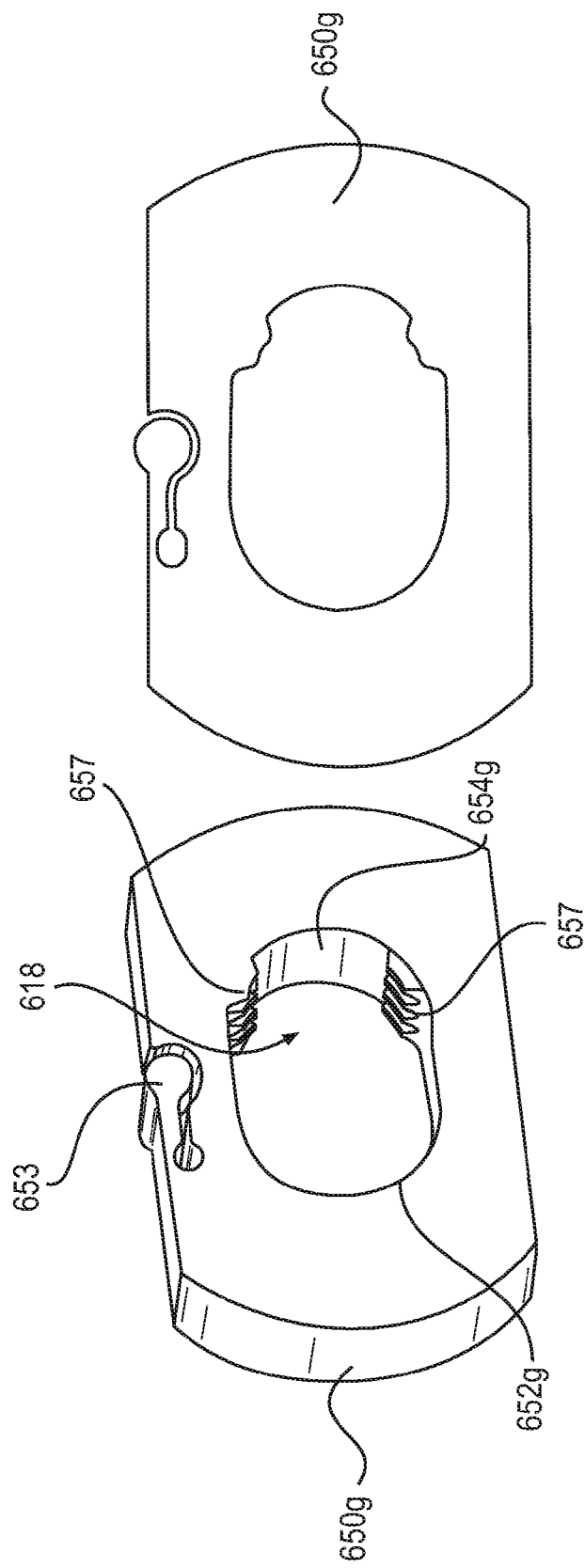

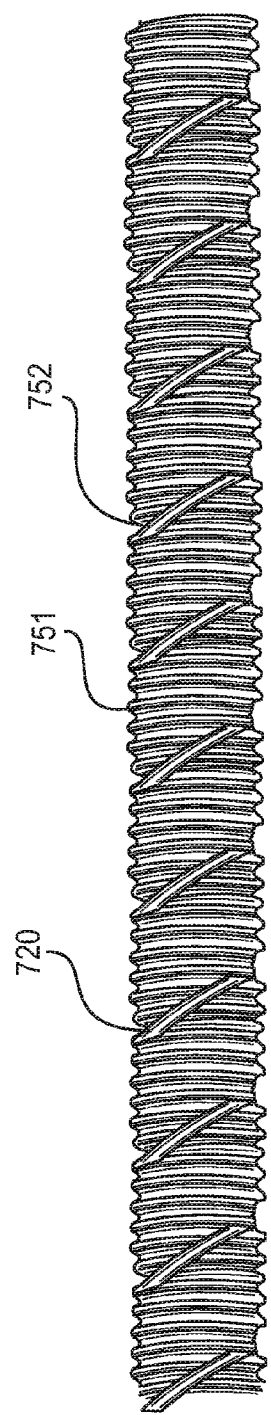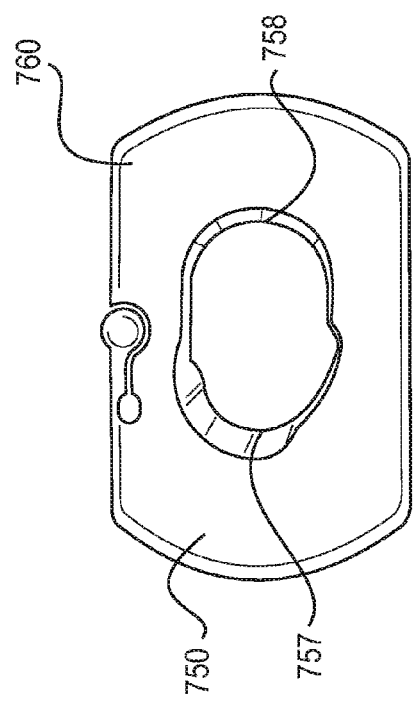
FIG. 9B
FIG. 9C

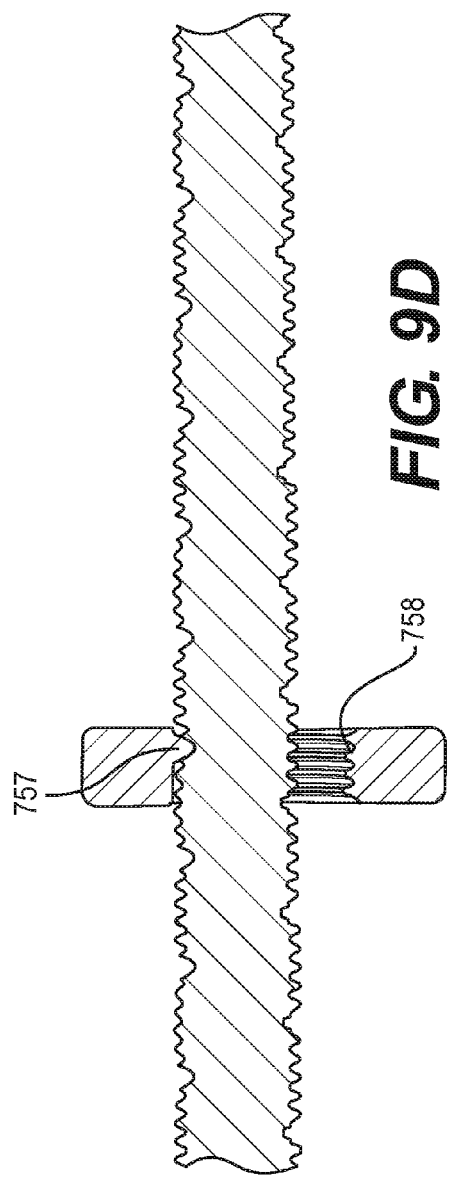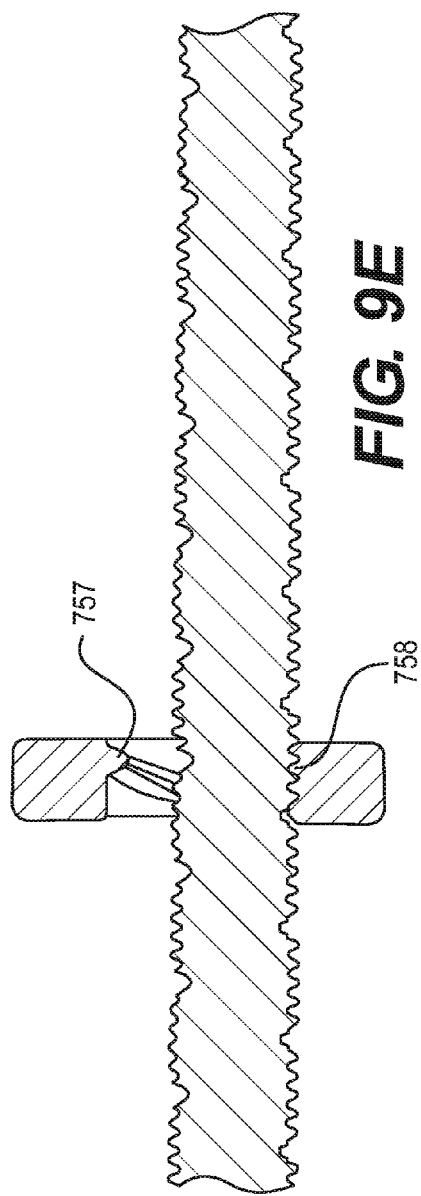

GRAFT DELIVERY SYSTEM AND METHODS THEREOF

CROSS-REFERENCE TO RELATED APPLICATIONS

The present application claims priority as a non-provisional application to U.S. Patent Application Ser. No. 61/862,833, filed Aug. 6, 2013, which is entitled "Graft Delivery System and Methods Thereof," which is incorporated herein by reference in its entirety.

FIELD OF THE INVENTION

The present invention relates to a delivery systems and methods for delivering biologic materials, including graft materials.

BACKGROUND OF THE INVENTION

In surgical procedures, a variety of biologic material can be delivered into a patient. Among these materials include graft material such as autograft, allograft and synthetic material. Accordingly, there is a need for delivery systems and methods that can effectively deliver such materials.

SUMMARY OF THE INVENTION

Systems and methods are provided for delivering material minimally invasively to a surgical site. In some embodiments, a system for spine surgery comprises a spacer positioned in a disc space, wherein the spacer includes an opening for receiving graft material therein. The system further comprises a minimally invasive delivery system for delivering material in and/or around the spacer. The delivery system includes a cannula comprising a proximal portion and a distal portion and a flexible shaft extending therethrough, wherein the flexible shaft includes an opening extending therethrough; a syringe threadingly attached to the proximal portion of the cannula, wherein the syringe includes a channel for receiving material therethrough and a removable handle; and an extrusion tool attached to the syringe, wherein the extrusion tool comprises a push handle, a threaded shaft for assisting in the extrusion material out of the syringe, and a receiving body, wherein the threaded shaft extends through the receiving body, and wherein the receiving body comprises an engagement mechanism including an opening therethrough, wherein the threaded shaft is capable of passing through the opening of the engagement mechanism in a first mode and a second mode, wherein in the first mode the threaded shaft can be pushed through the opening in the engagement mechanism without threading and in the second mode the threaded shaft can be pushed through the opening in the engagement mechanism with threading.

In other embodiments, a system for spine surgery comprises a spacer positioned in a disc space, wherein the spacer includes an opening for receiving graft material therein. The system further comprises a minimally invasive delivery system for delivering material in and/or around the spacer comprising a syringe including a channel for receiving material therethrough and a removable handle; and an extrusion tool attached to the syringe, wherein the extrusion tool comprises a push handle, a threaded shaft for assisting in the extrusion material out of the syringe, and a receiving body, wherein the threaded shaft extends through the receiving body, and wherein the receiving body comprises an engagement mechanism including an opening therethrough, wherein the threaded shaft is capable of passing through the opening of the engagement mechanism in a first mode and a second mode, wherein in the first mode the threaded shaft can be pushed through the opening in the engagement mechanism at a first rate and in the second mode the threaded shaft can be pushed through the opening in the engagement mechanism at a second rate, wherein the first rate is different from the second rate.

BRIEF DESCRIPTION OF THE DRAWINGS

The invention will be more readily understood with reference to the embodiments thereof illustrated in the attached drawing figures, in which:

FIG. 1 is a side view of a cannula in accordance with sonic embodiments.

FIG. 2 is a side view of a cannula with radio-opaque markers in accordance with some embodiments.

FIGS. 9A-9E are different views of components of a particular extrusion tool accordance with some embodiments.

Throughout the drawing figures, it should be understood that like numerals refer to like features and structures.

DETAILED DESCRIPTION OF THE INVENTION

Figure 3:
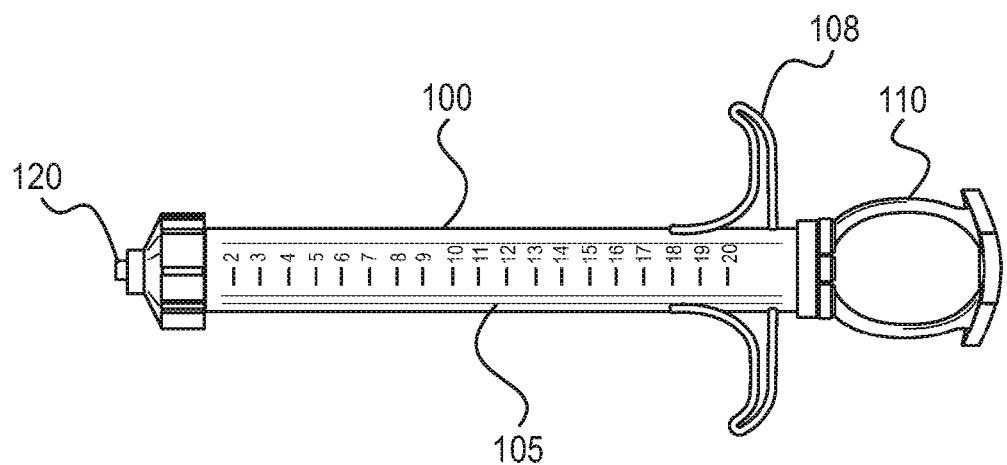
FIG. 3 is a side view of a syringe attachable to a cannula in accordance with some embodiments.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

In surgical procedures, a variety of material can be delivered into a patient. Among these materials include biological graft material such as autograft, allograft and synthetic material, as well as different types of cements. These materials can be delivered, for example, during a surgical procedure, such as a spinal fusion procedure. In some procedures, a spacer or cage can be delivered into a disc space, along with biological material to assist in fusion and bone growth.

A number of difficulties can arise during delivery of biologic material. First, it can be difficult to deliver materials minimally invasively through a small incision. In addition, it can be difficult to deliver materials from a great distance, which can be required by larger patient anatomy. Also, many systems do not accommodate multiple graft types (e.g., such as liquids or putties), nor do they allow for visualization during minimally invasive procedures. Furthermore, biologic material with greater viscosity can be difficult to extrude. Such material can then set or harden in a cannula or syringe prior to delivery, thereby clogging the instruments and making them difficult to clean.

To address these issues, a number of novel instruments are disclosed that operate alone or concurrently with each other to provide a number of benefits during material delivery. Advantageously, these instruments provide a means of minimally invasive delivery of material during a surgical procedure.

FIG. 1 is a side view of a cannula in accordance with some embodiments. The cannula 10 comprises a shaft 20 positioned between a proximal portion 40 and a distal portion 42. In some embodiments, the shaft 20 is stiff and rigid, while in other embodiments, the shaft 20 is flexible. The proximal portion 40 of the cannula 10 comprises a connection portion having internal threads. Advantageously, the proximal portion 40 can be connected to a distal end of a syringe (shown in FIG. 3) to form a minimally invasive delivery system. The distal portion 42 of the cannula 10 includes an opening for delivering material therethrough.

FIG. 2 is a side view of a cannula with radiopaque markers in accordance with some embodiments. Advantageously, the cannula 10 includes radiopaque markers 55 that are distributed along the length of the shaft 20 of the cannula 10. The radiopaque markers 55 render the cannula 10 opaque on a radiographic mage.

In some embodiments, the radiopaque markers 55 are in the form of radiopaque metal rings. In other embodiments, the radiopaque markers 55 are in the form of plastic rings. Advantageously, the radiopaque rings are distributed along a length of the shaft 20. In some embodiments, the radiopaque markers 55 are distributed such that they are spaced from one another, as shown in FIG. 2. In other embodiments, the radiopaque markers 55 are distributed such that they are closer and/or touching one another. The radiopaque markers 55 can occupy a majority of the body of the shaft 20, and in some embodiments, can cover the shaft 20 completely. The radiopaque markers 55 can be attached to the shaft 20 via an adhesive, such as tape or glue.

FIG. 3 is a side view of a syringe attachable to a cannula in accordance with some embodiments. The syringe 100 is attachable to the cannula 10 and includes a chamber 105 for receiving material, a removable handle 110 and a distal end 120. The chamber 105 comprises a cannula or tube for receiving material therein. In some embodiments, a proximal portion of the chamber 105 can include gripping members 108 which can be held by a surgeon to hold or stabilize the syringe 100 during use. The removable handle 110 can be used as a seal for the syringe 100, but can be removed to insert other instrumentation into the syringe 100 and/or cannula 10, such as the funnel shown in FIG. 4 or the mixing tool shown in FIG. 5. The distal end 120 of the syringe 100 includes a threaded portion which is configured to mate with the threads of the cannula 10.

Figure 4:
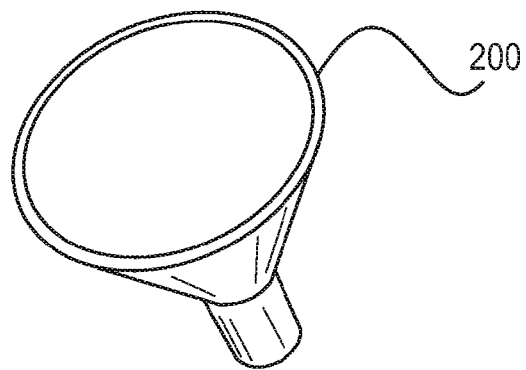
FIG. 4 is a top perspective view of a funnel for use with a syringe in accordance with some embodiments.

FIG. 4 is a top perspective view of a funnel for use with a syringe in accordance with some embodiments. The funnel 200 is provided to allow material to flow through the funnel 200 and into the syringe 100, thereby reducing spillage of the material.

Figure 5:
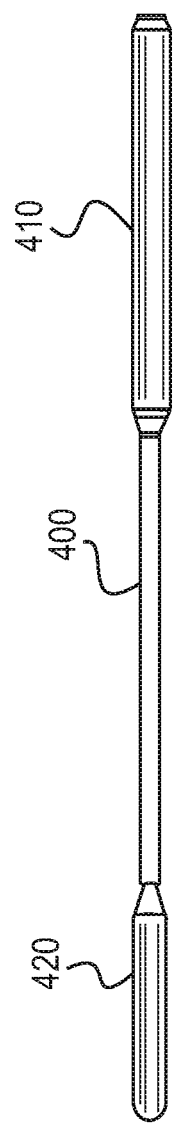
FIG. 5 is a side view of a mixing tool for use with a syringe in accordance with some embodiments.

FIG. 5 is a side view of a mixing tool for use with a syringe in accordance with some embodiments. The mixing tool 400 comprises a shaft having a narrow middle portion along with a thicker gripping end 410 and a thicker mixing end 420. The mixing tool 400 is configured to be inserted into the chamber 105 of the syringe 100 to assist in mixing material within the syringe.

Figure 6:
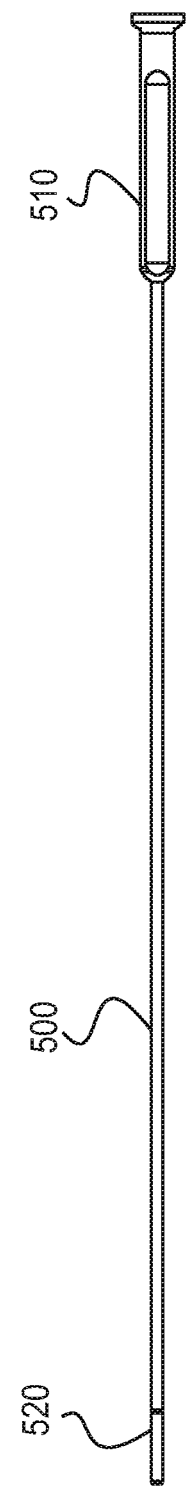
FIG. 6 is a side view of a pusher rod tool for use with a cannula in accordance with some embodiments.

FIG. 6 is a side view of a pusher rod tool for use with a cannula in accordance with some embodiments. The pusher rod tool 500 comprises a proximal handle portion 510 and a distal portion 520 that is sized to fit down the inner diameter of the cannula 10. The pusher rod tool 500 can be used to clean out any excess material that is left in the cannula 10 following material extrusion from the syring 100.

Figure 7:
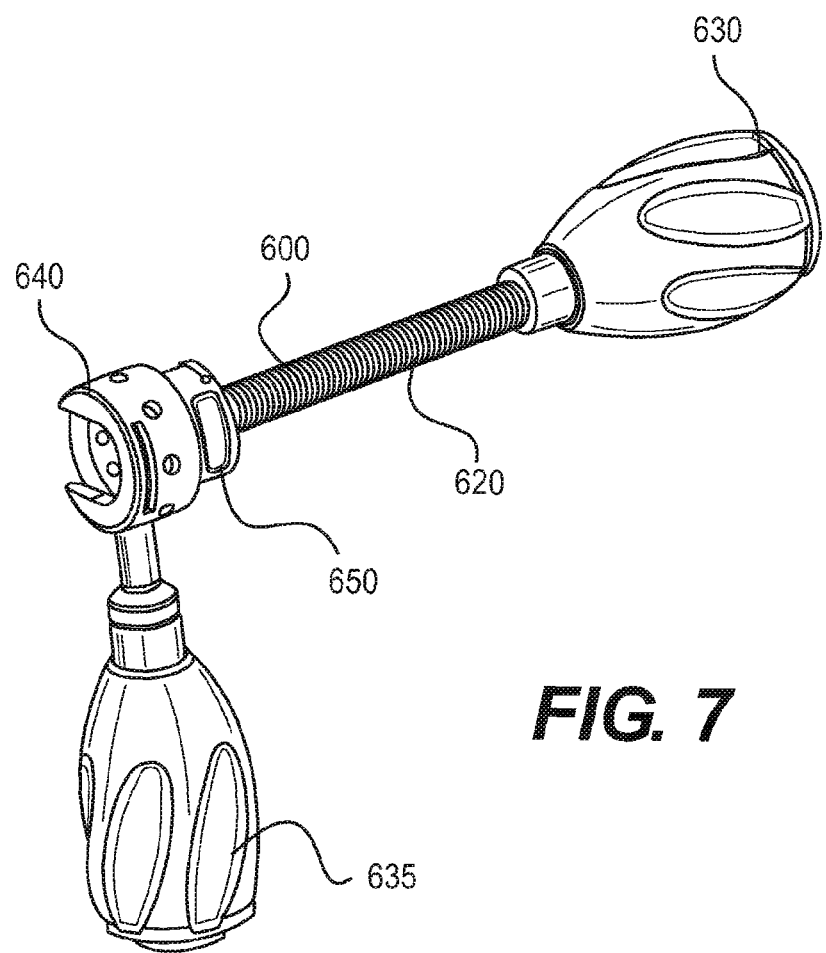
FIG. 7 is a top perspective view of an extrusion tool in accordance with some embodiments.

FIG. 7 is a top perspective view of an extrusion tool in accordance with some embodiments. The novel extrusion tool 600 comprises a threaded shaft 620, a push handle 630, a grip handle 635 and a receiving body 640. The extrusion tool 600 is designed to attach to a proximal end of the syringe 100, and is used to push material through the syringe. Advantageously, the extrusion toot 600 provides two modes upon which to extrude material out of the syringe. In a first mode, a user can simply apply a push force by grasping the push handle 630 to push the threaded shaft 620 through the body 640, such that a distal end of the threaded shaft 620 simply pushes material out of the syringe. In a second mode, a user can apply a combined rotational and push force by rotating the push handle 630 to thread the threaded shaft 620 through the body 640, such that a distal end of the threaded shaft applies an increased force to push material out of the syringe. The first mode can be used when material has relatively tow viscosity and is easy to extrude from the syringe and into the cannula, while the second mode can be used when material has relatively high viscosity and is more difficult to extrude from the syringe and into the cannula. To change between the two modes, the receiving body 640 includes an engagement mechanism 650 in the form of a button that can be used to convert the instrument from the first mode of operation to the second mode of operation, and vice versa.

The threaded shaft 620 has a proximal end that is attached to the push handle and a distal end that extends through the receiving body 640. In some embodiments, the threaded shaft 620 comprises a single thread pattern that extends along a length of the body of the shaft, as shown in FIG. 7. In other embodiments, the threaded shaft 620 comprises a multi-thread pattern that extends along a length of the body of the shaft, as shown in FIG. 9B. The thread pattern controls the rate of translational movement of the threaded shaft 620 as the threaded shaft 620 is rotatingly threaded (e.g., via rotation of the push handle 630 when the extrusion tool is in the second mode). Accordingly, when the threaded shaft 620 comprises a single thread pattern, the translational movement is relatively or completely constant upon each rotation of the shaft 620. When the threaded shaft 620 comprises a multi-thread pattern (e.g., two or more thread patterns), the rate of translational movement can vary depending on the thread pattern.

The push handle 630 is attached to a proximal end of the threaded shaft 620. The push handle 630 includes one or more gripping surfaces to aid in the gripping of the push handle 630.

The grip handle 635 extends downwardly from the receiving body 640, which receives the threaded shaft 620 therethrough. Like the push handle 630, the grip handle 635 can include one or more gripping surfaces to aid in the gripping of the grip handle 635. A surgeon can advantageously hold the grip handle 635 with a first hand and can use his other hand to push and/or rotate the push handle 630. In some embodiments, the grip handle is at a 90 degree angle relative to the threaded shaft 620 and the push handle 630. In other embodiments, the grip handle is an oblique angle relative to the threaded shaft 620 and the push handle 630.

The receiving body 640 comprises a proximal portion, a distal portion, and an opening or channel running from the proximal portion and the distal portion to accommodate the threaded shaft 620 therethrough. The proximal portion of the receiving body 640 includes an engagement button or mechanism 650 that is used to configure the mode of the extrusion tool 600. The engagement mechanism 650 (of which multiple variations are shown in FIGS. 8A-8G) includes an opening 618 therethrough through which the threaded shaft 620 can pass. As shown in FIG. 8A, the opening 618, which can be oval in shape, can be bounded by multiple side walls, such as sidewall 652 and an opposing sidewall 654. When the engagement mechanism 650 is pushed in one direction, the threaded shaft 620 will extend through the opening 618 at a location adjacent the sidewall 652. When the engagement mechanism 650 is pushed in the opposite direction, the threaded shaft 620 will extend through the opening 618 at a location adjacent the opposing sidewall 654. In some embodiments, as shown in FIG. 8A, sidewall 652 includes threads while opposing sidewall 654 does not includes threads. As such, to push threaded shaft 620 past the sidewall 652, the shaft 620 will need to be rotatingly threaded. To push the threaded shaft 620 past the opposing sidewall 654, only a pushing force need be applied. Accordingly, the engagement mechanism 650 controls the mode of operation of the extrusion tool 600, thereby controlling the rate of translation of the threaded shaft 620 and the amount of force of the threaded shaft 620 used to extrude material from the syringe and cannula.

The features on the engagement mechanism 650 control the rate of translational movement of the threaded shaft 620, and accordingly, control the amount of force that is applied to a material being extruded from the syringe and cannula. FIGS. 8A-8N illustrate several different types of engagement mechanisms 650. The engagement mechanisms 650 can be plate like members. While each of the engagement mechanisms 650 has different features to control the rate of translational movement of the threaded shaft 620 as it passes through the engagement mechanism, each of the engagement mechanisms 650 include a spring component 653 that engages one or more slots in the receiving body 640 to help maintain the engagement mechanism 650 in an engaged or disengaged position. For example, when the engagement mechanism 650 is positioned in a first mode (e.g., in a mode that allows the threaded shaft 620 to be pushed through the engagement mechanism 650 without threading), its spring component 653 is received in a slot within the receiving body 640 to thereby secure the engagement mechanism 650 in its current mode. To move the engagement mechanism 650 into the second mode (e.g., in a mode that allows the threaded shaft 620 to be pushed through the engagement mechanism 650 only via threading), the user applies a pushing force to the engagement mechanism 650, which disengages the spring component 653 from the slot. The engagement mechanism 650 can then be slid over until the spring component 653 rests in a different slot, thereby maintaining the engagement mechanism in the second mode.

Figure 8B:
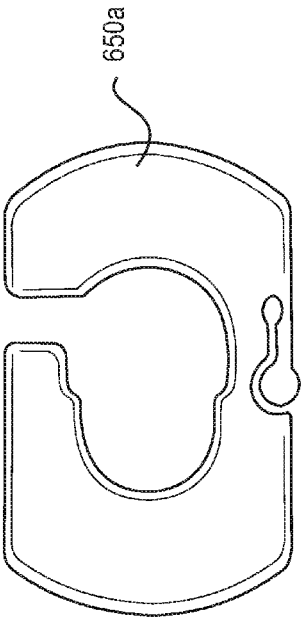
FIGS. 8A-8N are different views of an engagement mechanism of an extrusion tool in accordance with some embodiments.
Figure 8D:
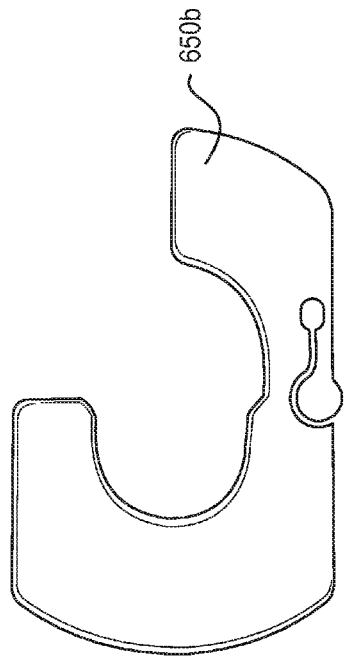
Figure 8A:
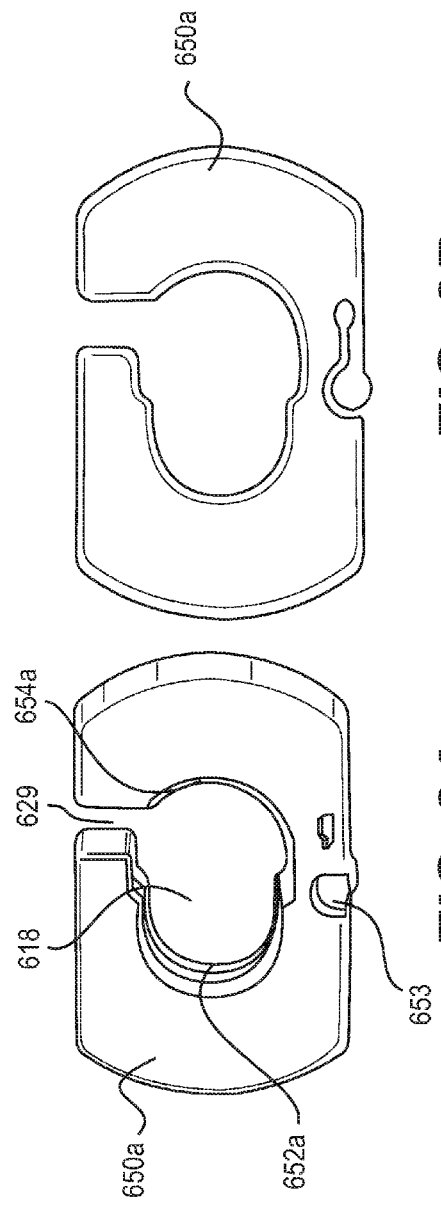

FIGS. 8A and 8B illustrate an engagement mechanism 650a having an opening 618 bounded by a sidewall 652a having a threads and a non-threaded sidewall 654a. In a first mode, the threaded shaft 620 passes adjacent the non-threaded sidewall 654a, and therefore, no threading is needed to push the threaded shaft 620 therethrough. In a second mode, the threaded shaft 620 passes adjacent the threaded sidewall 652a, and therefore, rotational threading is needed to push the threaded shaft 620 therethrough. A user can advantageously determine whether the extrusion tool 600 operates in the first mode or the second mode, simply by pushing the engagement mechanism 650. The opening 618 is not fully enclosed by a perimeter, as an upper slit 629 is formed through the upper wall of the engagement mechanism 650a.

Figure 8C:
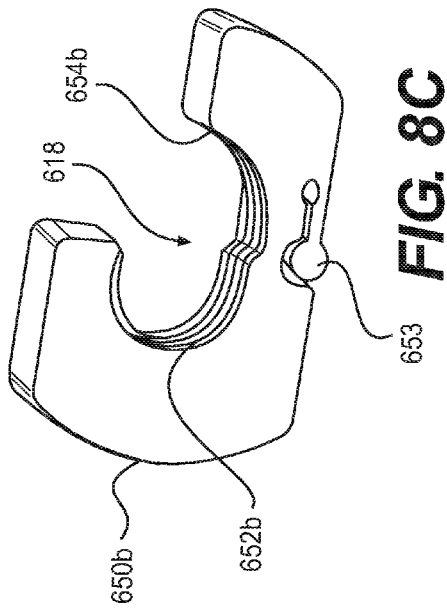

FIGS. 8C and 8D illustrate an engagement mechanism 650b having an opening 618 bounded by a sidewall 652b having threads and a non-threaded partial sidewall 654b. In a first mode, the threaded shaft 620 passes adjacent the non-threaded partial sidewall 654b, and therefore, no threading is needed to push the threaded shaft 620 therethrough. In a second mode, the threaded shaft 620 passes adjacent the threaded sidewall 652b, and therefore, rotational threading is needed to push the threaded shaft 620 therethrough. Like the opening in FIG. 8A, the opening 618 is not fully enclosed by a perimeter.

FIGS. 8E and 8F illustrate an engagement mechanism 650c having an opening 618 partially bounded by a partial sidewall 652c having threads and a non-threaded partial sidewall 654c. In a first mode, the threaded shaft 620 passes adjacent the non-threaded partial sidewall 654c, and therefore, no threading is needed to push the threaded shaft 620 therethrough. In a second mode, the threaded shaft 620 passes adjacent the threaded partial sidewall 652c, and therefore, rotational threading is needed to push the threaded shaft 620 therethrough. The upper surface of the opening 618 is unbounded by a perimeter, such that the opening 618 is completely exposed.

FIGS. 8G and 8H illustrate an engagement mechanism 650d having an opening 618 that is completely enclosed by a perimeter. The opening 618 is bounded by a non-threaded sidewall 652d and a partially threaded sidewall 654d on an opposing side. In a first mode, the threaded shaft 620 passes adjacent the non-threaded partial sidewall 652d, and therefore, no threading is needed to push the threaded shaft 620 therethrough. In a second mode, the threaded shaft 620 passes adjacent the threaded partially threaded sidewall 654d, and therefore, rotational threading is needed to push the threaded shaft 620 therethrough. The threads of the partially threaded sidewall 654d extend from an upper wall of the engagement mechanism 650d and continuously transition downwardly into the sidewall 654d.

FIGS. 8I and 8J illustrate an engagement mechanism 650e having an opening 618 that is also completely enclosed by a perimeter. Like the engagement mechanism in FIGS. 8G and 8H, the opening 618 is bounded by a non-threaded sidewall 652e and a partially threaded sidewall 654e. However, the threads on the sidewall 654e do not extend to an upper wall of the engagement mechanism.

FIGS. 8K and 8L illustrate an engagement mechanism 650f having an opening 618 that is also completely enclosed by a perimeter. The opening 618 is bounded by a threaded sidewall 652f and a non-threaded sidewall 654f. The threads of the threaded sidewall 652f are positioned in an opposite sidewall from the threads of the engagement mechanism in FIGS. 8I and 8J.

FIGS. 8M and 8N illustrate an engagement mechanism 650g having an opening 618 that is also completely enclosed by a perimeter. The opening 618 is bounded by a non-threaded sidewall 652g and a non-threaded sidewall 654g. However, two sets of threads 657 extend on each side of the non-threaded sidewall 654g—one set that rests on the upper wall of the engagement mechanism and one that rests on the lower wall of the engagement mechanism. In a first mode, the threaded shaft 620 passes adjacent the non-threaded sidewall 652g, and therefore, no threading is needed to push the threaded shaft 620 therethrough. In a second mode, the threaded shaft 620 passes adjacent the non-threaded sidewall 654g, and through the threads 657, such that rotational threading is needed to push the threaded shaft 620 therethrough.

With each of the engagement mechanisms 650 shown in FIGS. 8A-8N, a user can determine how fast to translate the threaded shaft, which serves as plunger to extrude material out of the syringe and cannula. The features on the engagement mechanism 650 provide an easy means to change the mode of operation of the extrusion tool, thereby giving a user the option to extrude less viscous material quickly using just a push force, or to extrude more viscous material more slowly using a rotational and push force.

Figure 9A:
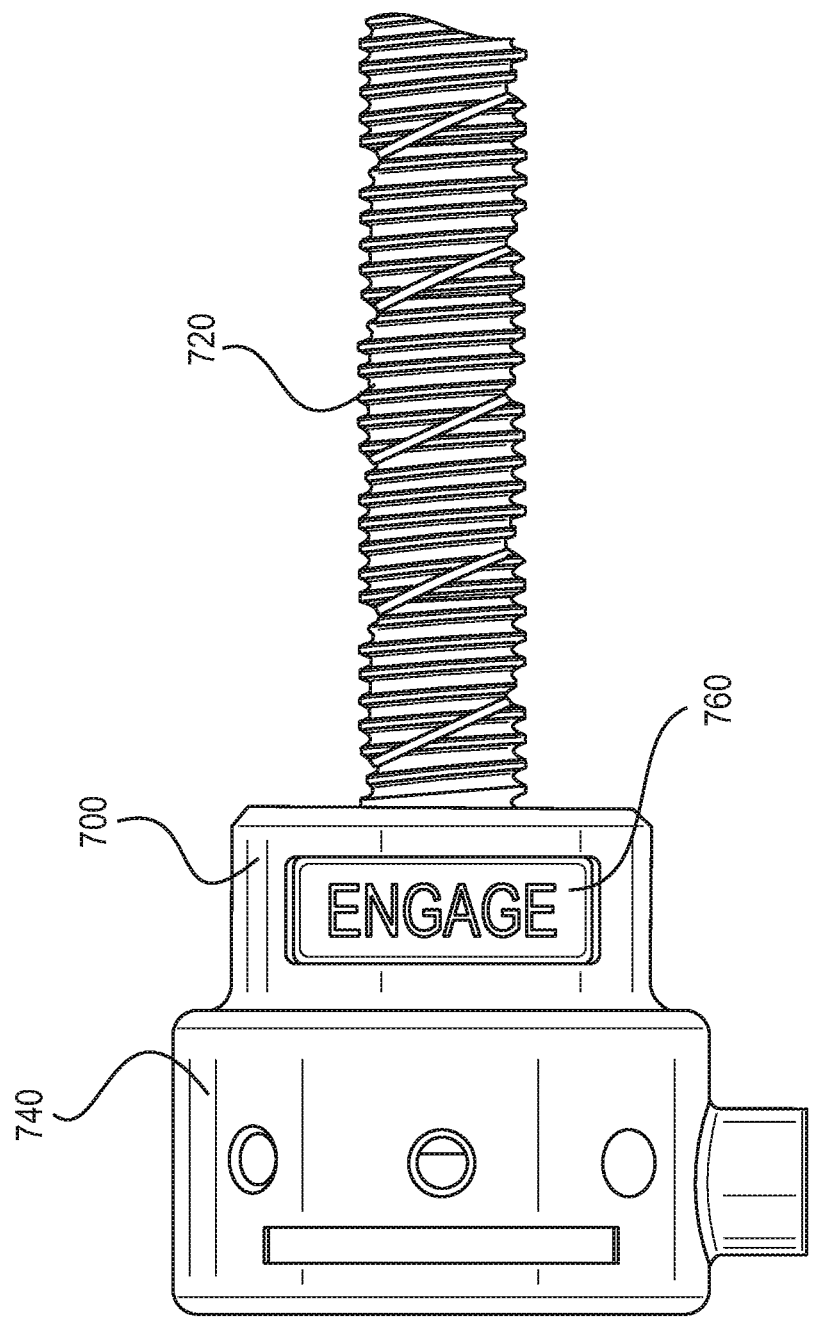

FIGS. 9A-9E are different views of components of a particular extrusion tool in accordance with some embodiments. The extrusion toot 700 includes similar features as the tool shown in FIG. 7, including a push handle (not shown), grip handle (not shown), threaded shaft 720 and a body 740 including an engagement mechanism 760. However, the threaded shaft 720 of the extrusion tool 700 has unique double patterned threading, which advantageously allows the rate of translation of the threaded shaft to change from one rate to another. As shown in FIG. 9C, the engagement mechanism 760 includes a sidewall 757 having features that accommodate the first pattern of threading and an opposing sidewall 758 having features that accommodate the second pattern of threading on the threaded screw.

FIG. 9B shows a close up view of the threaded shaft 720 having double patterned threading. The first thread pattern 751 includes threads having a relatively small thread pitch, while the second thread pattern 752 includes threads having a larger thread pitch. The position of the engagement mechanism 760 (shown in FIG. 9C) controls whether the threaded shaft 720 will translate forward along the first thread pattern 751 or the second thread pattern 752. The engagement mechanism 760 includes a sidewall 757 that accommodates the second thread pattern 752 and an opposing sidewall 758 that accommodates the first thread pattern 751. When the threaded shaft 720 passes adjacent the sidewall 757, the threaded shaft 720 will rotate along the second thread pattern 752 with the greater pitch (as shown in FIG. 9D), and therefore will translate a relatively long distance for each rotation of the shaft. When the threaded shaft 720 passes adjacent the sidewall 758 (as shown in FIG. 9E), the threaded shaft 720 will rotate along the first thread pattern 751 with the lesser pitch, and therefore will translate a relatively short distance for each rotation of the shaft. The extrusion tool in FIGS. 9A-9E thus provides an alternate way to change the rate of translation of the threaded shaft by using multiple thread patterns.

Figure 10:
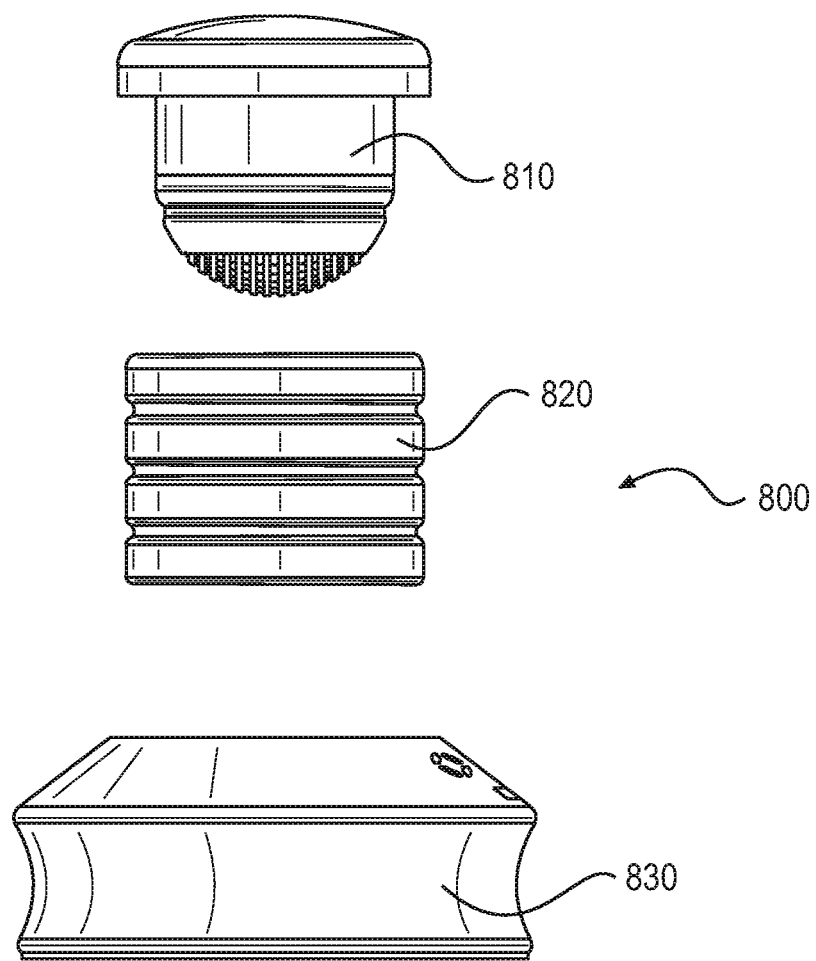
FIG. 10 is a side view of components of a bone morselizer tool in accordance with some embodiments.

FIG. 10 is a side view of components of a bone morselizer tool in accordance with some embodiments. The bone morselizer 800 can be used with any of the instruments described above, and includes three components: a bone crusher 810, a body 820 and a bone receiver 830. The bone receiver 830 is configured to receive autograft or allograft bone. The bone crusher 810 can then be used to crush and impact the hone until it is a desired size. The impacted bone can then be delivered to a surgical graft site.

The above systems and instruments can be used with a number of surgical procedures, including those using plates, spacers, rods and other stabilization devices. In some embodiments, a spacer can be inserted into a disc space as part of a fusion procedure. The spacer can be expandable or non-expandable, and can include an opening for receiving graft material therein. An example of an expandable spacer that can be used with the present systems and instruments include those found in U.S. patent application Ser. No. 14/326,513, filed Jul. 9, 2014, and herein incorporated by reference in its entirety. The instruments described above can be used to deliver bone graft material to the spacer minimally invasively, to thereby help with bone growth and fusion.

While the invention herein disclosed has been described by means of specific embodiments and applications thereof, numerous modifications and variations can be made thereto by those skilled in the art without departing from the scope of the invention as set forth in the claims.

What is claimed is:

1. A system for spine surgery comprising:
a spacer configured to be positioned in a disc space, wherein the spacer includes an opening for receiving graft material therein; and
a minimally invasive delivery system for delivering material in and/or around the spacer comprising:
a cannula comprising a proximal portion and a distal portion and a flexible shaft extending therethrough, wherein the flexible shaft includes an opening extending therethrough;
a syringe threadingly attached to the proximal portion of the cannula, wherein the syringe includes a channel for receiving material therethrough and a removable handle; and
an extrusion tool attached to the syringe, wherein the extrusion tool comprises a push handle, a threaded shaft for assisting in the extrusion material out of the syringe, and a receiving body,
wherein the threaded shaft extends through the receiving body, and wherein the receiving body comprises an engagement mechanism including an opening therethrough, wherein the threaded shaft is capable of passing through the opening of the engagement mechanism in a first mode and a second mode, wherein in the first mode the threaded shaft can be pushed through the opening in the engagement mechanism without threading and in the second mode the threaded shaft can be pushed through the opening in the engagement mechanism with threading, and
wherein the engagement mechanism includes a spring component that engages at least a slot in the receiving body in the first mode and is configured to be disengaged from the slot in the second mode.

2. The system of claim 1, wherein the extrusion tool comprises a grip handle.

3. The system of claim 2, wherein the grip handle is positioned at 90 degrees relative to the push handle.

4. The system of claim 1, wherein the engagement mechanism comprises an oval shaped opening.

5. The system of claim 1, wherein the opening of the engagement mechanism is completely enclosed by a perimeter.

6. The system of claim 1, wherein the opening of the engagement mechanism is partially enclosed by a perimeter.

7. The system of claim 1, wherein the opening of the engagement mechanism is bounded on one side by a threaded sidewall and on another side by a non-threaded sidewall.

8. The system of claim 7, wherein the threaded sidewall and the non-threaded sidewall oppose each other.

9. The system of claim 1, wherein the engagement mechanism comprises a push button.

10. The system of claim 1, wherein the spring component moves from a first position to a second position in order to move the threaded shaft in the second mode.

11. A system for spine surgery comprising:
a spacer configured to be positioned in a disc space, wherein the spacer includes an opening for receiving graft material therein; and
a minimally invasive delivery system for delivering material in and/or around the spacer comprising:
a syringe including a channel for receiving material therethrough and a removable handle; and
an extrusion tool attached to the syringe, wherein the extrusion tool comprises a push handle, a threaded shaft for assisting in the extrusion material out of the syringe, and a receiving body, wherein the threaded shaft extends through the receiving body, and wherein the receiving body comprises an engagement mechanism including an opening therethrough, wherein the threaded shaft is capable of passing through the opening of the engagement mechanism in a first mode and a second mode, wherein in the first mode the threaded shaft can be pushed through the opening in the engagement mechanism at a first rate and in the second mode the threaded shaft can be pushed through the opening in the engagement mechanism at a second rate, wherein the first rate is different from the second rate, and
wherein the engagement mechanism includes a spring component that engages at least a slot in the receiving body in the first mode and is configured to be disengaged from the slot in the second mode.

12. The system of claim 11, wherein the spacer is expandable.

13. The system of claim 11, further comprising a bone morselizer for impacting bone.

14. The system of claim 11, further comprising a cannula attachable to the syringe.

15. The system of claim 14, wherein the cannula comprises at least three radiopaque markers.

16. The system of claim 11, wherein the engagement mechanism comprises a plate with the opening passing therethrough.

17. The system of claim 11, wherein the opening of the engagement member is bounded on one side by a threaded sidewall and on an opposite side by a non-threaded sidewall.

18. The system of claim 11, wherein the spring component moves from a first position to a second position in order to move the threaded shaft in the second mode.

19. The system of claim 11, wherein the threaded shaft comprises dual thread patterns.

20. The system of claim 19, wherein when the engagement member engages the threaded shaft along a first thread pattern, the threaded shaft translates a first distance upon a single rotation of the threaded shaft, and wherein when the engagement member engages the threaded shaft along a second thread pattern, the threaded shaft translates a second distance upon a single rotation of the threaded shaft, wherein the first distance is different from the second distance.

\* \* \* \* \*